(12) United States Patent
Khan et al.

(10) Patent No.: US 12,161,637 B2
(45) Date of Patent: Dec. 10, 2024

(54) ANTI-CANCER GOLD COMPLEX, PROCESS OF SYNTHESIS AND METHOD OF TREATMENT THEREOF

(71) Applicant: King Saud University, Riyadh (SA)

(72) Inventors: Haseeb Ahmad Khan, Riyadh (SA); Abdullah Saleh Alhomida, Riyadh (SA); Ali Al-Hoshani, Riyadh (SA); Anvarhusein Abdulkadir Isab, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 17/957,476

(22) Filed: Sep. 30, 2022

(65) Prior Publication Data

US 2023/0087073 A1    Mar. 23, 2023

(51) Int. Cl.
A61K 31/444    (2006.01)
A61P 35/00     (2006.01)

(52) U.S. Cl.
CPC ............ *A61K 31/444* (2013.01); *A61P 35/00* (2018.01)

(58) Field of Classification Search
CPC .............................. A61K 31/444; A61P 35/00
See application file for complete search history.

(56) References Cited

U.S. PATENT DOCUMENTS

2011/0056561 A1* 3/2011 Burn ............... C09B 57/10
                                                 136/263
2021/0061818 A1* 3/2021 Isab ................ C07F 1/005

* cited by examiner

*Primary Examiner* — Jeffrey S Lundgren
*Assistant Examiner* — Alexander K. Showalter
(74) *Attorney, Agent, or Firm* — Kilpatrick Townsend & Stockton LLP

(57) ABSTRACT

The present disclosure relates generally to anti-cancer pharmaceuticals. More specifically, the disclosure is directed to gold complexes of Formula I with anti-cancer properties. The disclosure also provides a pharmaceutical composition comprising the complexes, a process of synthesizing the complexes and a method of treating cancer. The complexes of the present disclosure have a multi-target approach to cancer therapeutics by inducing cell apoptosis, cytotoxicity, mitochondrial membrane potential depolarization and increasing reactive oxygen species in cancer cells.

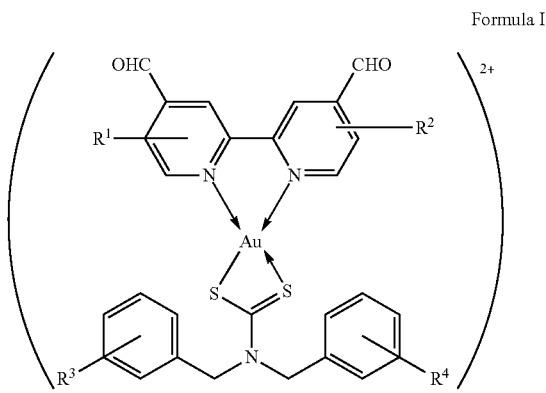

Formula I

12 Claims, 3 Drawing Sheets

Erlotinib
 Sorafenib
 Rosiglitazone
 DDBDG

ANTI-CANCER GOLD COMPLEX, PROCESS OF SYNTHESIS AND METHOD OF TREATMENT THEREOF

FIELD OF THE INVENTION

The present disclosure relates generally to anti-cancer pharmaceuticals. More specifically, the disclosure is directed to gold complexes of Formula I with anti-cancer properties. The disclosure also provides a pharmaceutical composition comprising the complexes, a process of synthesizing the complexes and a method of treating cancer.

DESCRIPTION OF THE RELATED ART

Background description includes information that may be useful in understanding the present invention. It is not an admission that any of the information provided herein is prior art or relevant to the presently claimed invention, or that any publication specifically or implicitly referenced is prior art.

Cancer is one of the most leading causes of death worldwide with the most common cancers being lung, breast, colorectal, prostrate and rectum cancer. Breast cancer is the most commonly diagnosed cancer. Among many chemotherapy drugs that are widely used for cancer treatment, cisplatin is one of the most compelling and effective ones against various types of cancers [Dasari S, Tchounwou P B. Cisplatin in cancer therapy: molecular mechanisms of action. Eur J Pharmacol. 2014; 740:364-378]. The FDA approval of platinum compound for cancer treatment in 1978 led to interest in platinum and other metal-containing compounds as potential anticancer drugs. Unfortunately, cisplatin treatment was found to be associated with drug resistance and many undesirable side effects including nephrotoxicity, cardiotoxicity, ototoxicity, immunosuppression, alopecia, and gastrointestinal disorders, which led to the search for other platinum analogs or combination therapies of cisplatin with other chemotherapy agents to overcome drug resistance and to minimize toxic effects [Wang X, Gou Z. Targeting and delivery of platinum-based anticancer drugs. ChemSoc Rev. 2013; 42:202-224; Rezaee R, Momtazi A A, Monemi A, Sahebkar A. Curcumin: A potentially powerful tool to reserve cisplatin-induced toxicity. Pharmacol Res. 2017; 117:218-227]. The cytotoxic effect of cisplatin is linked to the inhibition of replication by cisplatin-DNA adducts and induction of apoptosis [Siddik Z H. Cisplatin: mode of cytotoxic action and molecular basis of resistance. Oncogene. 2003; 22:7265-7279]. In addition, oxidative stress is also implicated as one of most important mechanisms in cisplatin toxicity while mitochondria are the primary target for cisplatin-induced oxidative stress causing reduction in mitochondrial membrane potential [Saad S Y, Najjar T A, Alashari M. Role of non-selective adenosine receptor blockade and phosphodiesterase inhibition in cisplatin-induced nephrogonadal toxicity in rats. ClinExpPharmacol Physiol. 2004; 31:862-867]. Excessive generation of reactive oxygen species (ROS) and poor antioxidant defense can result in apoptosis as well as necrosis in cancer cells [Hampton M B, Orrenius S. Dual regulation of caspase activity by hydrogen peroxide: implications for apoptosis. FEBS Lett. 1997; 414:552-556].

The development of novel metal-based compounds with pharmacological profiles different from platinum drugs is a major goal of current drug design and medicinal chemistry. In recent years, gold (III) complexes have gained increased attention due to their strong antitumor effects, generally by exploiting non-cisplatin-like mechanisms of action [Nardon C, Boscutti G, Fregona D. Beyond platinums: gold complexes as anticancer agents. Anticancer Res. 2014; 34:487-92; Kim J H, Ofori S, Parkin S, Vekaria H, Sullivancde P G, Awuah S G. Anticancer gold (III)-bisphosphine complex alters the mitochondrial electron transport chain to induce in vivo tumor inhibition. Chem Sci., 2021; 12:7467-79]. Interestingly, gold compounds form comparatively weaker interactions with DNA, suggesting that gold compounds exert their effects through some DNA-independent mechanisms [Nobili S, Mini E, Landini I, Gabbiani C, Casini A, Messori L. Gold compounds as anticancer agents: Chemistry, cellular pharmacology, and preclinical studies. Med Res Rev. 2010; 30:550-1128; Casini A, Hartinger C, Gabbiani C, Mini E, Dyson P J, Keppler B K, Messori L. Gold (III) compounds as anticancer agents: Relevance of gold-protein interactions for their mechanism of action. J InorgBiochem. 2008; 102: 564-575]. In contrast to platinum-based complexes that possess a greater tendency to permanently bind with DNA and produce irreversible platinum-DNA adducts, gold complexes exhibit reversible binding with DNA which is greatly influenced by the nature of gold-bound ligands [Marcon G, Messori L, Orioli P, Cinellu M A, Minghetti G. Reactions of gold (III) complexes with serum albumin. Eur J Biochem. 2003; 270:4655-4661; Maiore L, Cinellu M A, Nobili S, Landini I, Mini E, Gabbiani C, Messori L. Gold (III) complexes with 2-substituted pyridine as experimental anticancer agents: Solution behavior, reactions with model proteins, antiproliferative properties. J InorgBiochem. 2012; 108:123-127]. Recently Kim et al [Kim J H, Ofori S, Mertens R T, Parkin S, Awuah S G. Water-soluble Gold (III)-metformin complex alters mitochondrial bioenergetics in breast cancer cells. Chem Med Chem. 2021b; 16:3222-30] have synthesized new organogold (III) compounds supported by a diphenylphosphine benzene ligand that have shown stability toward biological thiols and demonstrated enhanced mitochondrial oxygen consumption rate as well as induced proton leakage in breast cancer cells. Moreover, the stability of gold compounds in physiological environment is crucial as it accounts for the successful delivery of the active moiety to the targeted sites [Yeo C I, Ooi K K, Tiekink E R T. Gold-based medicine: A paradigm shift in anti-cancer therapy? Molecules 2018; 23: 1410]. Cancer cells are known to undergo several pathway modifications in order to achieve uninterrupted cell proliferation, avoid apoptosis and support the metabolic requirements of the rapidly dividing cells. It is therefore imperative that novel drugs against multiple targets would be more effective for cancer treatment.

Thus there is a need in the art to provide novel metal containing anti-cancer compounds with high efficacy and multi-target therapeutics.

OBJECTS OF THE INVENTION

An object of the present disclosure is to provide gold based anti-cancer complexes with high therapeutic efficacy.

Another object of the present disclosure is to provide a process of synthesis of the complexes.

Yet another object of the present disclosure is to provide a method of treatment of cancer.

SUMMARY OF THE INVENTION

This summary is provided to introduce a selection of concepts in a simplified form that are further described below in Detailed Description section. This summary is not intended to identify key features or essential features of the claimed subject matter, nor is it intended to be used as an aid in determining the scope of the claimed subject matter.

In an aspect, the present disclosure provides an anti-cancer gold complex of Formula I, a stereoisomer, a pharmaceutically acceptable salt or a pharmaceutically acceptable solvate thereof:

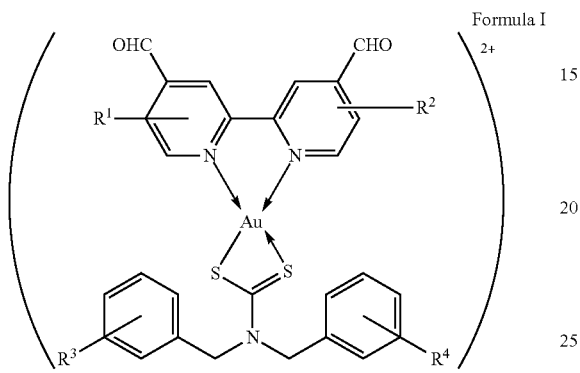

Formula I wherein $R^1$, $R^2$, $R^3$ and $R^4$ may be independently selected from one or more of H, —OH, $C_{1-6}$ alkoxy, $C_{1-6}$ alkyl, halogen, nitro, amino, —COOH, —$(C_{6-10})$aryl or —$(C_{4-14})$ heterocyclyl.

In a preferred embodiment, the complex is dibenzyldithiocarbamato-2,2'-bipyridine-4,4'-dicarboxaldehyde gold (III).

In another aspect, the present disclosure provides a pharmaceutical composition comprising an anti-cancer gold complex of Formula I, a stereoisomer, a pharmaceutically acceptable salt or a pharmaceutically acceptable solvate thereof.

In an embodiment, the composition may be a solid, liquid or semi-solid. In an embodiment, the composition may be a tablet, gel, capsule, solution, granules, powder, lozenge, suspension, suppositories, nanoparticles, oil, microparticles, or paste.

In another aspect, the disclosure provides an anti-cancer gold complex of the Formula I, a stereoisomer, a pharmaceutically acceptable salt or a pharmaceutically acceptable solvate thereof for the treatment of cancer.

In an aspect, the disclosure also provides use of the complex in the management of cancer. In an embodiment, the disclosure provides use of the complex as a medicament for chemotherapy.

In another aspect, the present disclosure provides a process of synthesis of an anti-cancer gold complex of Formula I, a stereoisomer, a pharmaceutically acceptable salt or a pharmaceutically acceptable solvate thereof, the process comprising the steps of: (a) mixing 2,2'-bipyridine-4,4'-dicarboxaldehyde compound (2) with Au(III) salt (3) in a solvent to generate a compound (4); and (b) adding and stirring a sodium dithiocarbamate compound (5) into the solution of step (a) to give a complex of Formula I.

General Scheme I

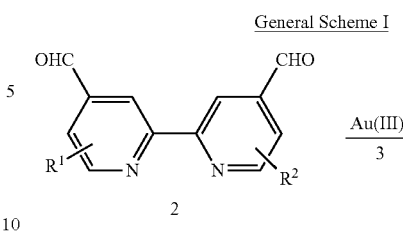

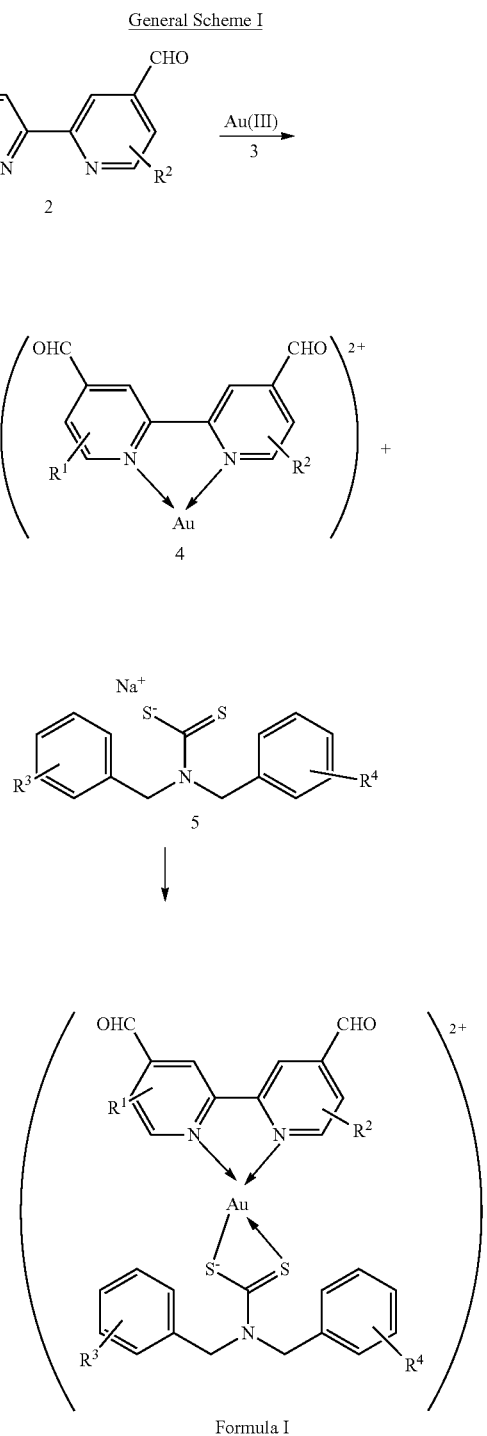

Formula I

In an embodiment, the Au(III) salt may be selected from sodium tetrachloroaurate, potassium tetrachloroaurate, sodium tetracyanoaurate, potassium tetracyanoaurate, or combinations thereof.

In yet another aspect, the present disclosure provides a method of treatment of a subject by administering a therapeutically effective amount of an anti-cancer gold complex of Formula I, a stereoisomer, a pharmaceutically acceptable salt or a pharmaceutically acceptable solvate thereof:

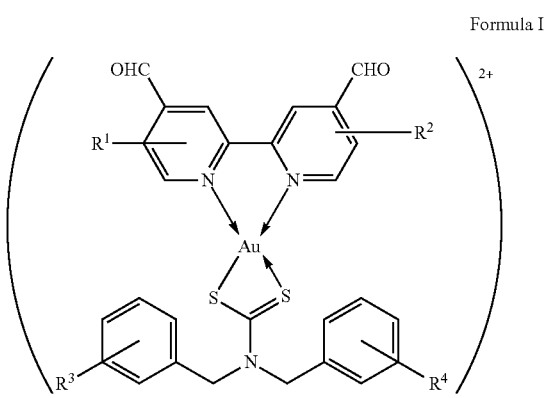

Formula I wherein $R^1$, $R^2$, $R^3$ and $R^4$ have the definitions as recited above.

Other aspects of the invention will be set forth in the description which follows, and in part will be apparent from the description, or may be learnt by the practice of the invention.

BRIEF DESCRIPTION OF THE DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION OF THE INVENTION

Figure 1:
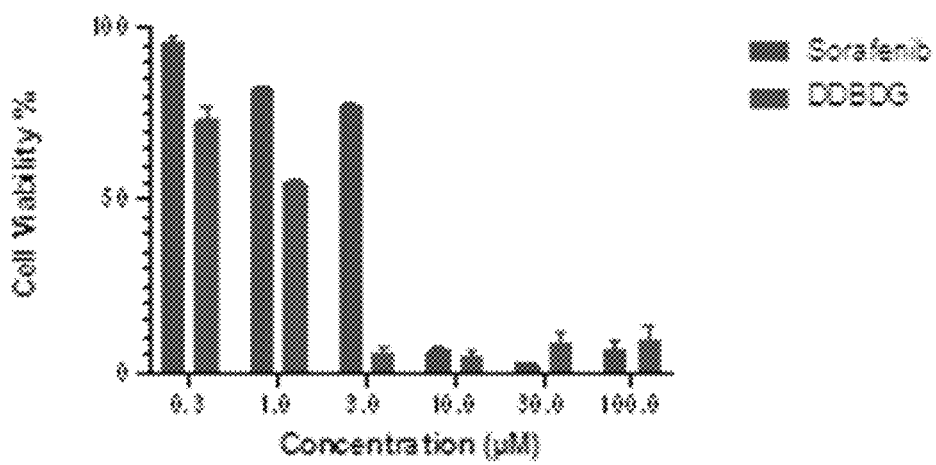
FIG. 1 graphically provides cytotoxicity in MCF-7 breast cancer cell line by variation in percentage cell viability (%) with concentrations of 0.3, 1, 3, 10, 30, and 100 µM of (a) Sorafenib, and (b) gold complex (DDBDG) as per an exemplary embodiment of the present disclosure.

The following is a detailed description of embodiments of the disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some embodiments, numbers have been used for quantifying weights, percentages, ratios, and so forth, to describe and claim certain embodiments of the invention and are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Various terms as used herein are shown below. To the extent a term used in a claim is not defined below, it should be given the broadest definition persons in the pertinent art have given that term as reflected in printed publications and issued patents at the time of filing.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context requires otherwise, throughout the specification which follow, the word "comprise" and variations thereof, such as, "comprises" and "comprising" are to be construed in an open, inclusive sense that is as "including, but not limited to."

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified.

The description that follows, and the embodiments described therein, is provided by way of illustration of an example, or examples, of particular embodiments of the principles and aspects of the present disclosure. These examples are provided for the purposes of explanation, and not of limitation, of those principles and of the disclosure.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The term "or", as used herein, is generally employed in its sense including "and/or" unless the content clearly dictates otherwise.

The term, "$(C_{1-6})$alkyl", as used herein, refers to saturated aliphatic groups, including straight or branched-chain alkyl groups having six or fewer carbon atoms in its backbone, for instance, $C_1$-$C_6$ for straight chain and $C_3$-$C_6$ for branched chain. As used herein, $(C_{1-6})$alkyl refers to an alkyl group having from 1 to 6 carbon atoms. Representative examples of alkyl include, but are not limited to, methyl, ethyl, n-propyl, n-butyl, n-pentyl, n-hexyl, isopropyl, sec-butyl, isobutyl, tert-butyl, isopentyl, 2-methylbutyl and 3-methylbutyl.

Furthermore, unless stated otherwise, the alkyl group can be unsubstituted or substituted with one or more substituents, for example, from one to four substituents, independently selected from the group consisting of halogen, hydroxy, cyano, nitro and amino. Examples of substituted alkyl include, but are not limited to hydroxymethyl, 2-chlorobutyl, trifluoromethyl and aminoethyl.

The term, "$(C_{1-6})$alkoxy" refers to a $(C_{1-6})$alkyl having an oxygen attached thereto. Representative examples of alkoxy groups include, but are not limited to, methoxy, ethoxy, propoxy, isopropoxy, n-butoxy, isobutoxy and tert-butoxy. Furthermore, unless stated otherwise, the alkoxy groups can be unsubstituted or substituted with one or more groups. A substituted alkoxy refers to a $(C_{1-6})$alkoxy substituted with one or more groups, particularly one to four groups independently selected from the groups indicated above as the substituents for the alkyl group.

The term "$(C_{6-10})$aryl" or "aryl" as used herein refers to monocyclic or bicyclic hydrocarbon groups having 6 to 10 ring carbon atoms, wherein at least one carbocyclic ring is having a π electron system. Examples of $(C_{6-10})$aryl ring systems include, but are not limited to, phenyl and naphthyl. Unless indicated otherwise, aryl group can be unsubstituted or substituted with one or more substituents, for example 1-4 substituents independently selected from the group consisting of halogen, $(C_{1-6})$alkyl, hydroxy, cyano, nitro, —COOH, amino and $(C_{1-6})$alkoxy.

The term, "$(C_{4-14})$heterocyclyl", as used herein refers to a 4- to 14-membered, saturated, partially unsaturated or unsaturated monocyclic or bicyclic ring system containing 1 to 4 heteroatoms independently selected from the group consisting of oxygen, nitrogen and sulfur. Saturated heterocyclic ring systems do not contain any double bond, whereas partially unsaturated heterocyclic ring systems contains at least one double bond, and unsaturated heterocyclic ring systems form an aromatic system containing heteroatom(s). The oxidized form of the ring nitrogen and sulfur atom contained in the heterocyclyl to provide the corresponding N-oxide, S-oxide or S,S-dioxide is also encompassed in the scope of the present disclosure. Representative examples of heterocyclyls include, but are not limited to, tetrahydrofuran, tetrahydrothiophene, pyrrolidine, dihydropyran, tetrahydropyran, thio-dihydropyran, thio-tetrahydropyran, piperidine, piperazine, morpholine, 1,3-oxazinane, 1,3-thiazinane, 4,5,6-tetrahydropyrimidine, 2,3-dihydrofuran, dihydrothiene, dihydropyridine, tetrahydropyridine, isoxazolidine, pyrazolidine, furan, pyrrole, thiophene, imidazole, oxazole, thiazole, triazole, tetrazole, benzofuran, indole, benzoxazole, benzothiazole, isoxazole, triazine, purine, pyridine, pyrazine, quinoline, isoquinoline, phenazine, oxadiazole, pteridine, pyridazine, quinazoline, pyrimidine, isothiazole, benzopyrazine and tetrazole. Unless stated otherwise, $(C_{4-14})$heterocyclyl can be unsubstituted or substituted with one or more substituents, for example, substituents independently selected from the group consisting of oxo, halogen, hydroxy, cyano, nitro, amine, $(C_{1-6})$alkyl and COOH.

The term, "halogen" as used herein refers to chlorine, fluorine, bromine or iodine atom.

As described herein, the term 'therapeutically effective amount' refers to the amount of the complex or its composition required to bring about a change or improvement in a subject without adverse side effects or overdosing.

The term, 'subject' as used herein refers to an animal, preferably a mammal, and most preferably a human. The term 'mammal' used herein refers to warm-blooded vertebrate animals of the class 'mammalia', including humans, characterized by a covering of hair on the skin and, in the female, milk-producing mammary glands for nourishing the young, the term mammal includes animals such as cat, dog, rabbit, bear, fox, wolf, monkey, deer, mouse, pig and human.

The term, 'management', or 'treatment' as used herein refers to alleviate, slow the progression, attenuation, prophylaxis or as such treat the existing disease or condition. Treatment also includes treating, preventing development of, or alleviating to some extent, one or more of the symptoms of the diseases or condition. Management or treatment of cancer includes decreasing, stabilizing or preventing tumor cell division, proliferation or metastasis; induction of apoptosis, maintaining the cell size, decreasing tumor cell size, or reduction in cancer induced mortality.

Aspects of the present disclosure provide novel gold complexes with anti-cancer activity against cancers including, but not limited to, breast cancer, rectal cancer, lung cancer, liver cancer, leukemia, colon cancer, stomach cancer, prostrate cancer, testicular cancer, bone cancer, brain cancer, oral cancer, pancreatic cancer, among others.

In an embodiment, the present disclosure provides an anti-cancer gold complex of Formula I, a stereoisomer, a pharmaceutically acceptable salt or a pharmaceutically acceptable solvate thereof:

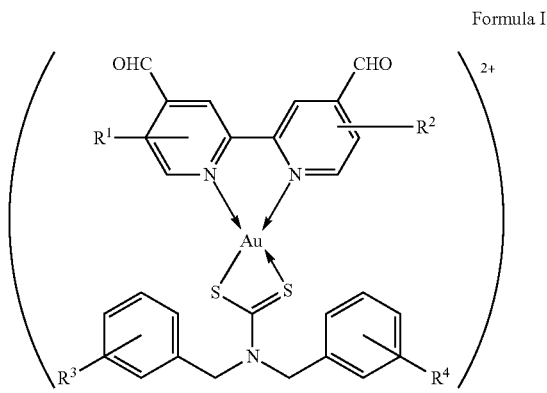

Formula I wherein $R^1$, $R^2$, $R^3$ and $R^4$ may be independently selected from one or more of H, —OH, $C_{1-6}$ alkoxy, $C_{1-6}$ alkyl, halogen, nitro, amino, —COOH, —$(C_{6-10})$aryl or —$(C_{4-14})$ heterocyclyl.

In an embodiment, $R^1$, $R^2$, $R^3$ and $R^4$ may be independently selected from one or more of H, —OH, —$OCH_3$, —$OC_2H_5$, —$CH_3$, —$C_2H_5$, Cl, Br, nitro, amino, phenyl, or COOH.

In a preferred embodiment, the complex is dibenzyldithiocarbamato-2,2'-bipyridine-4,4'-dicarboxaldehyde gold (III).

In an embodiment, the complex of Formula I can be converted into a pharmaceutically acceptable salt. The pharmaceutical acceptable salts of the complex of Formula I according to the disclosure are prepared in a manner known to one skilled in the art.

In an embodiment, the complex with cationic charge may form a salt with pharmaceutically acceptable counter ions including acetate, benzene sulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts. Any other well known counter ion may be employed.

In another embodiment, the present disclosure provides a pharmaceutical composition comprising an anti-cancer gold complex of Formula I, a stereoisomer, a pharmaceutically acceptable salt or a pharmaceutically acceptable solvate thereof.

In an embodiment, the composition may further comprise a pharmaceutically acceptable excipient, carrier or additive. In an embodiment, excipient may include, but is not limited to, a diluent, binder, disintegrant, glidant, lubricant, fillers, antioxidants, dispersants, emulsifiers, surfactant, stabilizers, preservatives, defoamers, flavors, solubilizers, coating material or the like, which is non-toxic, and inert, which does not have undesirable effects on a subject to whom it is administered and is suitable for delivering a therapeutically active agent to the target site without affecting the therapeutic activity of the said agent.

The present disclosure also relates to a process for the production of the pharmaceutical composition, which includes bringing a complex of Formula I, into a suitable administration form using a pharmaceutically acceptable excipient or a carrier and, if appropriate, further suitable a pharmaceutically acceptable additives or auxiliaries. The pharmaceutical compositions containing the complex of Formula I according to the disclosure are prepared in a manner known to one skilled in the art.

In an embodiment, the composition may be a solid, liquid or semi-solid. In an embodiment, the composition may be a tablet, gel, capsule, solution, granules, powder, lozenge, elixirs, suspension, suppositories, nanoparticles, oil, microparticles, or paste.

In an embodiment, the pharmaceutical compositions can be administered orally, for example in the form of pills, tablets, coated tablets, capsules, granules, powders or elixirs. Administration, however, can also be carried out rectally, for example in the form of suppositories, or parenterally, for example intravenously, intramuscularly or subcutaneously, in the form of injectable sterile solutions or suspensions, or topically, for example in the form of ointments or creams or transdermally, in the form of patches, or in other ways, for example in the form of aerosols or nasal sprays (nasally). However any other mode or administration well known in the art may be employed. In preferred embodiments, the pharmaceutical compositions may be administered orally.

For the production of oral dosages form of the complex of Formula I such as the pills, tablets, coated tablets and hard gelatin capsules, it is possible to use, for example, lactose, corn starch or compounds thereof, cellulose compounds, gum *arabica*, magnesia or glucose, etc. Pharmaceutically acceptable excipients that can be used for soft gelatin capsules and suppositories are, for example, fats, waxes, natural or hardened oils, etc. Suitable pharmaceutically acceptable excipients for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the said solvents.

The compositions may be formulated to have different release rates such as immediate release, controlled release or sustained release.

In another embodiment, the pharmaceutical compositions normally contain about 1% to 99%, for example, about 5% to 70%, or from about 10% to about 30% by weight of the comp ex of Formula I. The amount of the complex of Formula I in the pharmaceutical compositions normally is from about 5 to 500 mg or may be lower than or higher than the lower and the upper limit respectively.

In another embodiment, the disclosure provides an anti-cancer gold complex of Formula I, a stereoisomer, a pharmaceutically acceptable salt or a pharmaceutically acceptable solvate thereof for the treatment of cancer.

In an embodiment, the disclosure also provides use of the complex in the management of cancer.

The complex has a multi-target therapeutic activity in that it is effective via multiple routes including, causing cell apoptosis, disrupting mitochondrial membrane potential, and generating potentially toxic reactive oxidation species (ROS) to increase oxidative stress.

Gold compounds have been reported to inhibit the proliferation of cancer cells by targeting mitochondrial function resulting in disruption of the electron transport chain accompanied by disruption of mitochondrial membrane permeability [Bhabak K P, Bhuyan B J, Mugesh G. Bioinorganic and medicinal chemistry: Aspects of gold (I)-protein complexes. Dalton Trans. 2011; 40:2099-2111]. The alteration of mitochondrial membrane potential results in the accumulation of ROS which promotes lipid peroxidation and the activation of the p38-MAPK apoptosis pathway [Wang B, Jiang H, Ma N, Wang Y. Phosphorylated-p38 mitogen activated kinase expression is associated with clinical factors in invasive breast cancer. Springer plus 2016; 5:934-940] that triggers the activation of initiator caspases including caspase-3, caspasse-6 and caspase-7, together with the activation of DNase for DNA fragmentation leading to cell death [Park S J, Kim I S. The role of p38 MAPK activation in auranofin-induced apoptosis of human promyelocytic leukemia HL-60 cells. Br J Pharmacol. 2015; 146:506-513].

PPARγ is a transcription factor which gets activated when a ligand binds to it. It has been reported that PPARγ regulates transcription of genes involved in differentiation of cells, proliferation, angiogenesis, apoptosis, organ formation, inflammation, and energy metabolism [Desvergne B, Wahli W. Peroxisome proliferator-activated receptors: nuclear control of metabolism. Endocr Rev. 1999; 20:649-88; Theocharis S, Margeli A, Vielh P, Kouraklis G. Peroxisome proliferator-activated receptor-gamma ligands as cell-cycle modulators. Cancer Treat Rev. 2004; 30:545-54; Shashni B, Sakharkar K R, Nagasaki Y, Sakharkar M K. Glycolytic enzymes PGKI and PKM2 as novel transcriptional targets of PPARγ in breast cancer pathophysiology. J Drug Target. 2013; 21:161-174]. The presence of PPAR-responsive regulatory elements site in the promoter region of two enzymes involved in the ATP generation steps in glycolysis has been documented whereas the activation of PPARγ decreased the activities of those enzymes and inhibited cell proliferation [Shashni B, Sharma K, Singh R, Sakharkar K R, Dhillon S K, Nagasaki Y, Sakharkar M K. Coffee component hydroxyl hydroquinone (HHQ) as a putative ligand for PPAR gamma and implications in breast cancer. BMC Genomics 2013; 14 (Suppl 5): S6]. Tumor cells show changes in expression of cell cycle and growth regulating proteins influenced by PPARγ activators including thiazolidinediones and tyrosine based activators that can inhibit cell growth and promote apoptotic activity in cancer cells [Vignati S, Albertini V, Rinaldi A, Kwee I, Riva C, Oldrini R, Capella C, Bertoni F, Carbone G M, Catapano C V. Cellular and molecular consequences of peroxisome proliferator-activated receptor gamma activation in ovarian cancer cells. Neoplasia. 2006; 8:851-861].

Activation of PPAR-γ plays an inhibitory role in cell growth and proliferation by affecting cell differentiation. These properties make PPAR-γ activation by natural or synthetic ligands an attractive pharmacological tool in cancer prevention and treatment. The complexes of the present disclosure can activate PPAR-γ. In some embodiments, the complex of the present disclosure may outperform known PPARγ agonists including Erlotinib, Sorafenib and Rosiglitazone in terms of binding energy and the number of residues involved in hydrogen bonds with the receptor.

In some embodiments, high concentrations of the complex are equipotent to conventionally used Sorafenib however low concentrations of the complex have higher cytotoxicity in cancer cells than same concentration of Sorafenib. This suggests the effectiveness of lower doses of the complex. The present complex also causes significantly higher apoptosis in cancer cells, higher cytotoxicity, is more potent in disruption of mitochondrial membrane potential and generates higher ROS. The more potent activity of the complex will reduce the dosage needed and can reduce the costs of chemotherapy drastically making it accessible to everyone.

In an embodiment, the disclosure provides use of the complex as a medicament for chemotherapy.

The complexes of the present disclosure are not irritants nor do they have mutagenic, tumorigenic or reproductive toxicity. It does not cross the blood brain barrier.

In an embodiment, the complex of the present disclosure may be used along with other therapeutic agents. In an embodiment, the combination of complex of present disclosure with another therapeutic agent or treatment includes co-administration of a complex of Formula I with the other therapeutic agent or treatment as either a single combination dosage form or as multiple, separate dosage forms, administration of the complex of the present disclosure first, followed by the other therapeutic agent or treatment and administration of the other therapeutic agent or treatment first, followed by the complex of present disclosure.

In another embodiment of the present disclosure, the other therapeutic agent may be any agent that is known in the art to treat, prevent, or reduce the symptoms of a disease or disorder. The selection of other therapeutic agent(s) is based upon the particular disease or disorder being treated. Such choice is within the knowledge of a treating physician. Furthermore, the additional therapeutic agent may be any agent when administered in combination with the administration of a complex of the present disclosure provides benefit to the subject in need thereof. In particular embodiments, the other therapeutic agent may be a chemotherapeutic agent.

In another embodiment, the present disclosure provides a process of synthesis of an anti-cancer gold complex of the Formula I, a stereoisomer, a pharmaceutically acceptable salt or a pharmaceutically acceptable solvate thereof, the process comprising the steps of: (a) mixing 2,2'-bipyridine-4,4'-dicarboxaldehyde compound (2) with Au(III) salt (3) in a solvent to generate a compound (4); and (b) adding and stirring a sodium dithiocarbamate compound (5) into the solution of step (a) to give a complex of Formula I.

General Scheme I

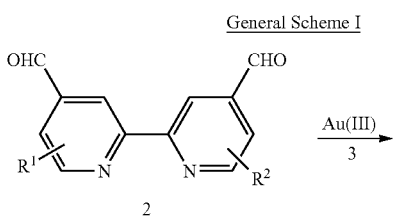

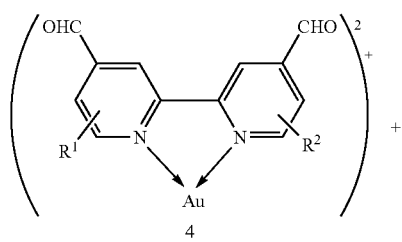

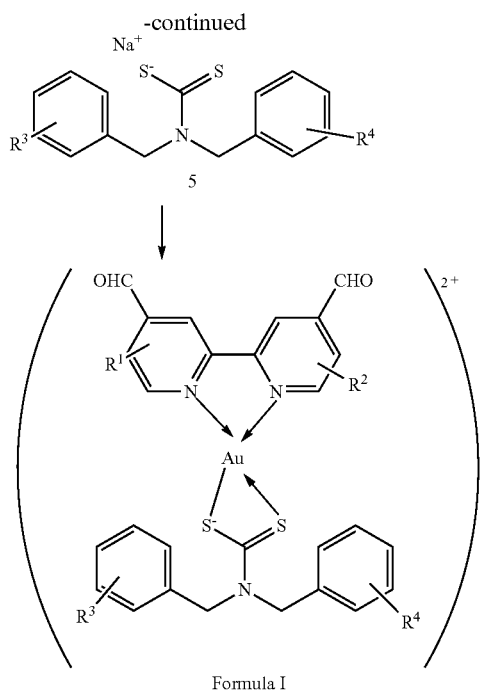

Formula I

In an embodiment, the solvent may be selected from ethanol, methanol, water, propanol, dimethylsulfoxide, or combinations thereof, preferably the solvent is ethanol.

In an embodiment, before mixing the 2,2'-bipyridine-4,4'-dicarboxaldehyde compound in the solvent it may be dissolved separately in an organic solvent. In some embodiments, the organic solvent may be dichloromethane, benzene, xylene, toluene, or combinations thereof; preferably the solvent is dichloromethane.

In an embodiment, the mixing of step (a) may be performed for about 2 to about 5 hours, preferably for about 3 hours. In an embodiment, the stirring of step (b) may be performed for about 30 minutes to about 3 hours, preferably for about an hour. The stirring or mixing may be performed by a magnetic stirrer, rotary shaker or any other technique or instrument well known in the art.

In an embodiment, the Au(III) salt may be selected from sodium tetrachloroaurate, potassium tetrachloroaurate, sodium tetracyanoaurate, potassium tetracyanoaurate, or combinations thereof.

In an embodiment, the process maybe performed at ambient temperature conditions. The complex obtained from step (b) may be further filtered to remove any insolubles, evaporated to remove any excess solvent to give crude product and further may be purified by any method known in the art.

In an embodiment, the process may give a yield of at least 50%, at least 60%, at least 70%, at least 80% or at least 90%.

In an embodiment, the present disclosure provides a method of treatment of a subject by administering a therapeutically effective amount of an anti-cancer gold complex of the Formula I, a stereoisomer, a pharmaceutically acceptable salt or a pharmaceutically acceptable solvate thereof.

The therapeutically effective amount or dose of the complex of Formula I, which is to be administered, can cover a wide range depending on the type of disease or disorder to be treated. The dose to be administered daily is to be selected to suit the desired effect. A suitable dosage is about 0.01 to 100 mg/kg of the complex of Formula I depending on the body weight of the subject per day, for example, about 0.1 to 50 mg/kg/day of a complex of Formula I. If required, higher or lower daily doses can also be administered.

The selected dosage level will depend upon a variety of factors including the activity of the complex of the present disclosure, or its salt employed, the route of administration, the time of administration, the rate of excretion of the particular complex being administered, the duration of the treatment, other concurrently administered drugs, compounds and/or materials, the age, sex, weight, condition, general health and prior medical history of the patient (subject) being treated, and like factors well known in the medical arts.

In an embodiment, the cancer may be breast cancer, rectal cancer, prostrate cancer, brain cancer, ovarian cancer, lung cancer, colorectal cancer, colon cancer, multiple myeloma, leukemia, cervical cancer, stomach cancer, skin cancer, thyroid cancer, testicular cancer, bone cancer, bladder cancer, intestinal cancer, or pancreatic cancer; particularly breast cancer.

While the foregoing describes various embodiments of the disclosure, other and further embodiments of the disclosure may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

EXAMPLES

The present invention is further explained in the form of following examples. However, it is to be understood that the following examples are merely illustrative and are not to be taken as limitations upon the scope of the invention.

Materials and methods: All organic ligands were purchased from Sigma-Aldrich and gold salts from Strom Chemicals USA. Breast cancer cell lines MCF-7 were obtained from American Type Culture Collection, ATCC (Virginia, USA). Dulbecco's Modified Eagle's Medium (DMEM), Fetal Bovine Serum (FBS), and 0.25% Trypsin 0.1% EDTA were obtained from Gibco (Grand Island, NY). The 3-(4,5-dimethylthiazol-2-yl)-2,5-diphenyltetrazolium bromide (MTT) and DMSO were purchased from Sigma-Aldrich (St. Louis, MO).

Statistical analysis: Data were analyzed by one-way ANOVA followed by Dunnett's multiple comparison test. P values<0.05 were considered as statistically significant.

Example 1: Synthesis and Characterization of Gold Complex

The synthesis of dibenzyldithiocarbamato-2,2'-bipyridine-4,4'-dicarboxaldehyde gold (III) (abbreviated as DDBDG, 1) was conducted in two sequential steps (Scheme 2). In the first step, 0.106 g (0.500 mmol) 2,2'-bipyridine-4,4'-dicarboxaldehyde (2) in 10 mL dichloromethane was added to 0.200 g (0.500 mmol) Na[AuCl$_4$]·2H$_2$O (3) in 10 mL ethanol and the mixture was stirred for 3 h, generating a yellow solution (4). In the second step, 0.500 mmol of the sodium dibenzyldithiocarbamate (DBDTC, 5) in 5 mL ethanol was added drop-wise to the above mixture. The mixture was stirred for an additional 1 hr resulting in the formation of orange color precipitate of the gold complex DDBDG.

The product was collected by filtration, washed with distilled water (3×10 mL) and dried under vacuum. Yield obtained was 77%.

Scheme 2

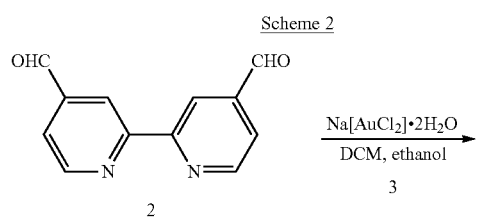

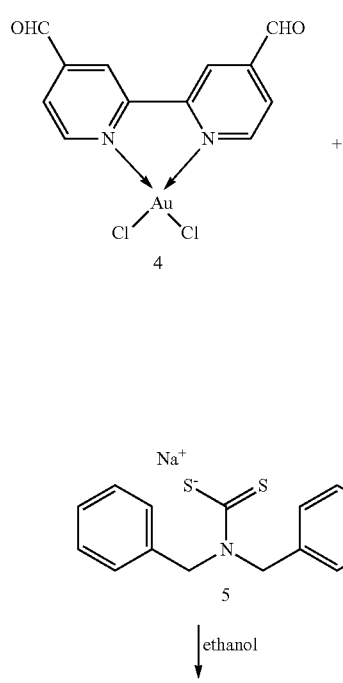

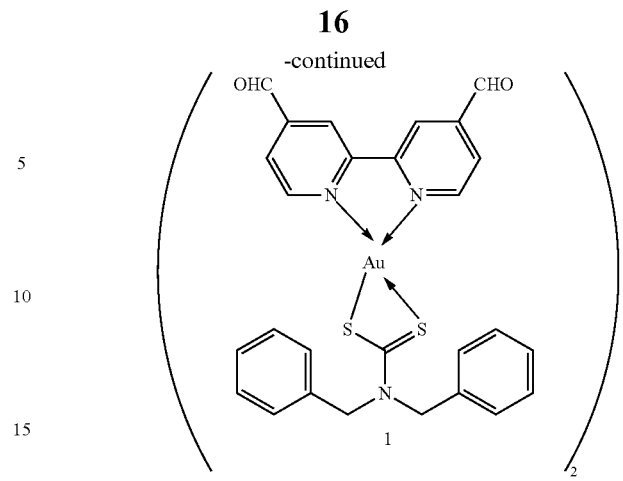

Elemental analysis was performed on Perkin Elmer Series 11 (CHNS/O) Analyzer 2400. The solid-state FT-IR spectra were recorded on a Nicolet FT-IR spectrophotometer, over the range 4000-400 cm$^{-1}$ at resolution 4.00 cm$^{-1}$. The $^1$H and 13C NMR spectra were recorded on a JEOL-LA 500 NMR spectrophotometer, operating at 500.0 and 125.65 MHz, respectively, corresponding to a magnetic field of 11.74 T. The spectral conditions included 32 k data points, 3.2 s acquisition time, and 5.75 us pulse width. 13C NMR spectra were obtained with 1H broadband decoupling and following spectral conditions: 32 k data points, 1.0 s acquisition time, 2.5 s pulse delay, and 5.12 us pulse width. All spectra were recorded at 297 K in CDCl$_3$ relative to tetramethylsilane (TMS) as an internal standard. The Mid-IR frequencies, $^1$H NMR chemical shifts and $^{13}$C NMR chemical shifts of free ligands and DDBDG complex are given in Tables 1, 2 and 3 respectively.

TABLE 1

| Mid-IR frequencies (cm$^{-1}$) for free ligand and DDBDG | | | | | Stretch |
|---|---|---|---|---|---|
| Ligand\complex | | | | C—N | S—C=S |
| DMDTC | — | — | 1397 | 1488 | 926 |
| DEDTC | — | — | 1347 | 1445 | 986 |
| DBDTC | 1600 | 2923, 2854 | 1436 | 1467 | 985 |
| DDBDG | 1707 | 2935, 2854 | 193.4 | 1537 | 1067, 904 |

TABLE 2

| $^1$H NMR chemical shifts for free ligand and their complexes in DMSO | | | | | | | |
|---|---|---|---|---|---|---|---|
| Ligand\complex | H-1 | H-2 | H-4 | H-6 | H-8 | H-9 | Aromatic-Hs |
| DMDTC | — | — | — | — | 3.35 s | — | 45.7 |
| DEDTC | — | — | — | — | 3.93 q | 1.13 t | — |
| DBDTC | — | — | — | — | 5.31, 4.77 d | — | 7.24 m-7.39 m |
| DDBDG | 9.01 d | 7.91 d | 8.80 s | 10.19 | 5.00, 5.03 d | — | 7.30 m-7.39 m |

TABLE 3

| $^{13}$C NMR chemical shifts for free ligand and their complexes in DMSO | | | | | | | | | |
|---|---|---|---|---|---|---|---|---|---|
| Ligand\complex | C1 | C2 | C3 | C4 | C5 | C6 | C7 | C8 | C9 | Aromatic-Cs |
| DMDTC | — | — | — | — | — | — | 208.3 | 45.7 | — | — |
| DEDTC | — | — | — | — | — | — | 206.4 | 49.5 | 12.1 | — |

TABLE 3-continued

¹³C NMR chemical shifts for free ligand and their complexes in DMSO

| Ligand\complex | C1 | C2 | C3 | C4 | C5 | C6 | C7 | C8 | C9 | Aromatic-Cs |
|---|---|---|---|---|---|---|---|---|---|---|
| DBDTC | — | — | — | — | — | — | 213.1 | 56.9 | — | 127.7-137.2 |
| DDBDG | 142.8 | 119.4 | 155.9 | 122.8 | 151.2 | | 193.4 | 58.3 | — | 127.8-135.9 |

DMDTC = sodium dimethyl dithiocarbamate and DEDTC = Sodium diethyldithiocarbamate

Example 2: Cell Viability Analysis

Cell viability was determined by 3-(4,5-dimethylthiazol-2-yl)-2,5-diphenyltetrazolium bromide (MTT) assay. Breast cancer cells, MCF-7, were seeded in a 96-well tissue culture plate at 10,000 cells/well in 200 μl of DMEM. The cells were treated with DDBDG and Sorafenib at final concentrations of 0.3, 1, 3, 10, 30, and 100 μM for 24 h. Then, 20 μl of MTT (5 mg/mL) was added to the each well and incubated in a $CO_2$ incubator at 37° C. in the dark for 3 h. After incubation, a purple-colored formazan dye is produced and appeared as dark crystals in the bottom of the wells. To dissolve the formazan crystals, the culture medium was discarded and 100 μL of isopropanol were added to each well. The absorbance was recorded at 570 nm against reagent blank. The cell viability was calculated by the formula below:

Cell viability (%)=[Absorbance Compound/Absorbance DMSO]*100

The results of the cell viability assay for the DDBDG and Sorafenib are presented in FIG. 1. The results of cytotoxicity showed the survival of the cells as a function of concentration of DDBDG and Sorafenib, with the respective $IC_{50}$ values of 0.875 μM and 4.445 μM. At lower concentration, DDBDG was more potent than Sorafenib for tested cell line while their toxicities were comparable at higher concentrations.

Example 3: Apoptosis Analysis

The apoptotic effects of DDBDG and sorafenib on MCF-7 breast cancer cell line were studied using Muse® Annexin V Live & Dead Cell Kit. MCF-7 cells were seeded in 6 well plates at 1.5×10⁴ cells per well. After 24 hours of incubation at 37° C. and 5% $CO_2$ under 95% humidified environment, cells were treated with DDBDG and sorafenib at final concentrations of 1, 3, and 10 μM for 24 h. DMSO was used as a negative control. The final DMSO concentration in each well was less than 0.1%. The harvested cells were stained with Annexin V-FITC and Dead Cell reagent following the manufacture's protocol. Then, the percentage of apoptotic cells was estimated by flow cytometry.

Figure 2:
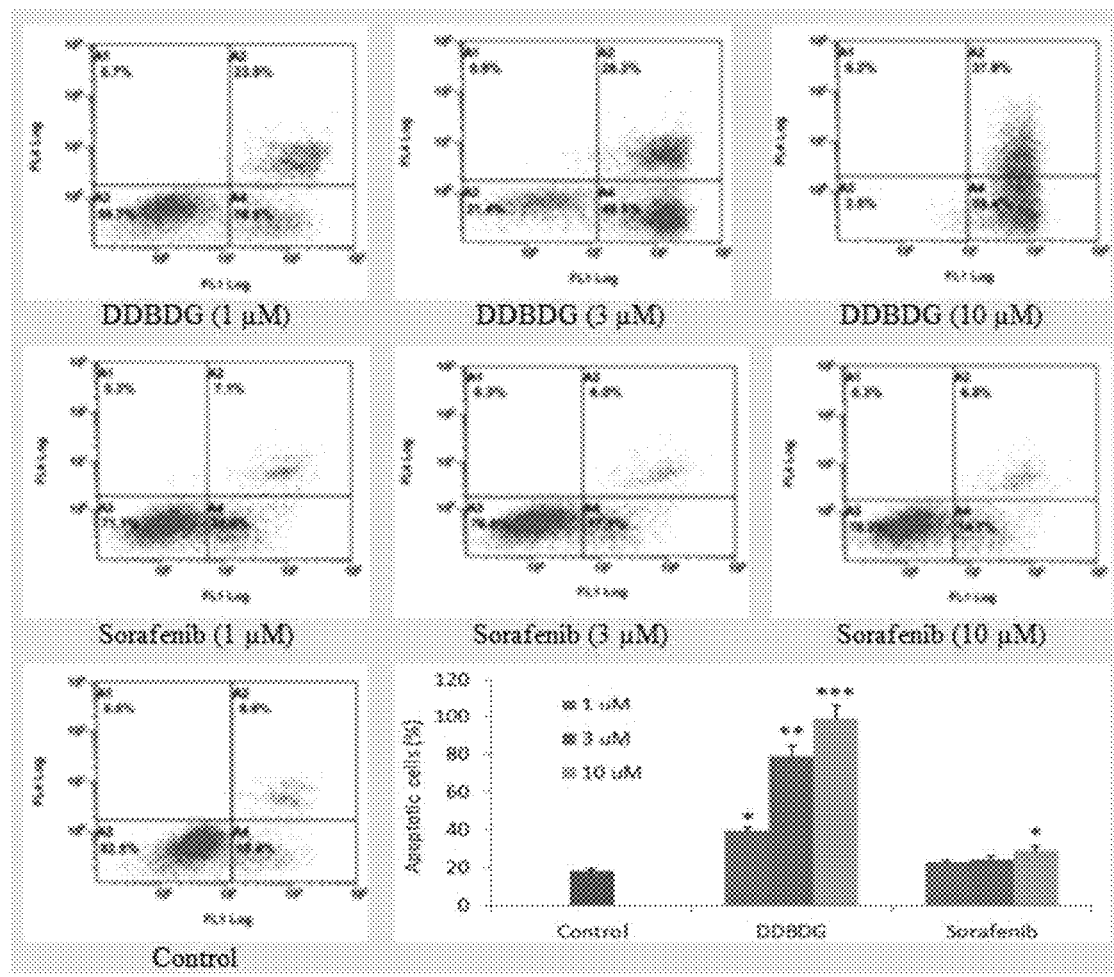
FIG. 2 depicts comparative evaluation of apoptotic effects in cancer cells for (a) Sorafenib, and (b) gold complex (DDBDG) as per an exemplary embodiment of the present disclosure. Bar chart shows the combined both early and late apoptosis. *$P<0.05$, $P<0.01$ and *$P<0.001$ versus control group.

Results of the apoptosis analysis are provided in FIG. 2. The results of apoptosis analysis showed that DDBDG induced 2.2 folds, 4.4 folds, and 5.5 folds apoptosis for 1 μM, 3 μM, and 10 μM concentrations, respectively. While the induction of apoptosis for Sorafenib was found to be 1.2-folds (1 μM), 1.3-folds (3 μM) and 1.6-folds (10 μM). These findings clearly indicate that DDBDG induced significantly higher apoptotic effects as compared to known PPARγ agonist and anti-cancer drug, Sorafenib.

Example 4: Mitochondrial Membrane Potential Analysis

Mitochondrial membrane potential is an important parameter to assess the integrity of mitochondria, which is a potential target in cancer therapeutics. The loss of mitochondrial membrane potential has been known to be associated with early stages of apoptosis and reactive oxygen species (ROS) induction. To assess the mitochondrial membrane potential, Muse® MitoPotential Kit (Luminex, IL, USA) was used. MCF-7 cells were seeded in a 6 well plate at 1.5×10⁴ cells/well. After 24 hours of incubation at 37° C. and 5% $CO_2$ under 95% humidified environment, cells were treated with DDBDG and Sorafenib at final concentrations of 1 and 5 μM for 24 h. DMSO was used as a negative control. The final DMSO concentration in each well was less than 0.1%. Then, cells were stained with MitoPotential reagents following the manufacture's protocol. The percentage of depolarized/live cells was estimated by flow cytometry.

Figure 3:
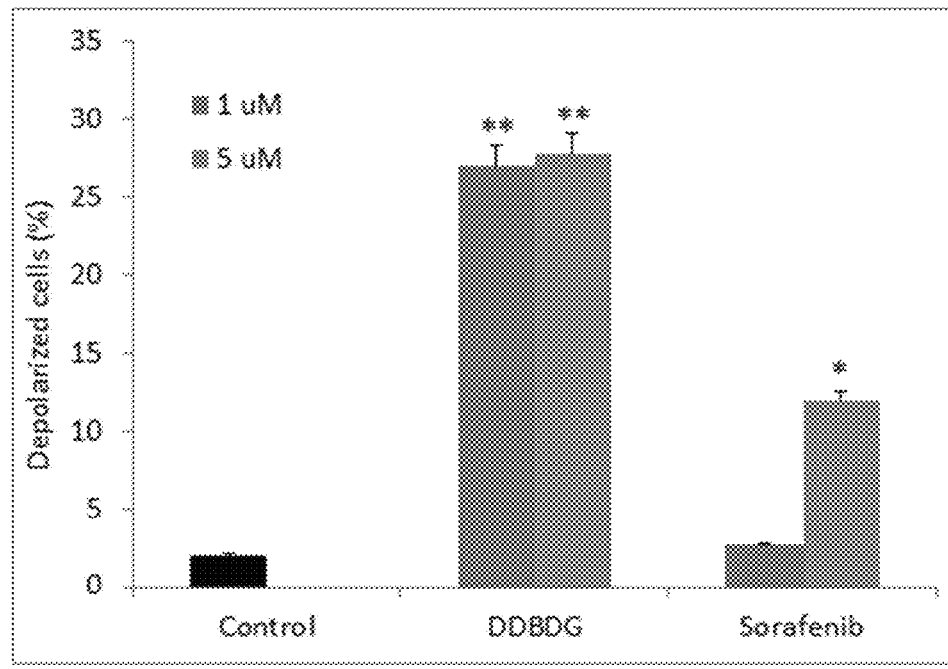
FIG. 3 graphically provides effects on mitochondrial membrane potential depolarization in cancer cells as a factor of percentage depolarization cells (%) at concentrations of 1 and 5 µM of (a) Sorafenib, and (b) gold complex (DDBDG) as per an exemplary embodiment of the present disclosure. *$P<0.01$ and **$P<0.001$ versus control group FIG. 4 graphically compares percentage reactive oxygen species (%) generated by concentrations of 1 and 5 µM of (a) Sorafenib, and (b) gold complex (DDBDG) as per an exemplary embodiment of the present disclosure. *$P<0.01$ and **$P<0.001$ versus control group.

The results of the effects of the samples on the mitochondrial membrane potential depolarization in cancer cell line are provided in FIG. 3. The mitochondrial membrane potential was significantly depolarized by DDBDG, roughly three-folds higher compared to positive control Sorafenib. In higher concentration, DDBDG and Sorafenib depolarized cancer cells in percentages of 27.8% and 12.0%, respectively. In lower concentration, cancer cells depolarization by DDBDG and Sorafenib was 27.0% and 2.7%, respectively.

Example 5: Oxidative Stress Analysis

The induction of oxidative stress via ROS generation endogenously in cancer cells is a potential target of anticancer agents. Oxidative stress causes irreversible cellular damage which induces apoptosis in concentration-dependent manner. MCF-7 cells were plated at 1.5×10⁴ cells/well using a 6 well plate to estimate the generation of reactive oxygen species (ROS). After 24 hours of incubation at 37° C. and 5% $CO_2$ under 95% humidified environment, cells were treated with DDBDG and Sorafenib at final concentrations of 1 and 5 μM for 24 h. DMSO was used as a negative control. The final DMSO concentration in each well was less than 0.1%. Then, the cells were harvested and stained with Muse® Oxidative Stress Kit (Luminex, IL, USA) following the manufacture's protocol. The percentage of cells that were undergoing oxidative stress was measured by flow cytometry.

Figure 4:
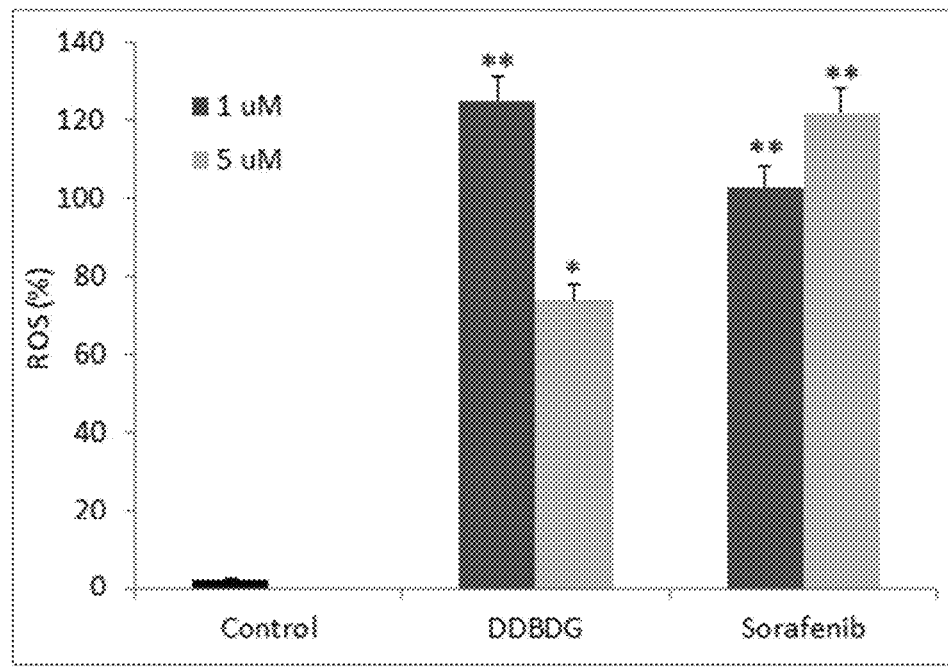

The effect of the samples on the generation of reactive oxygen species (ROS) in cancer cell line is provided in FIG. 4. The % ROS was higher for DDBDG at lower concentration of 1 μM compared to Sorafenib. In low concentration of 1 μM, DDBDG and Sorafenib increased ROS generation by 125.53% and 73.76%, respectively. With concentration of 5 μM, ROS generations were 103.47% and 122.11%, respectively.

Example 6: Molecular Docking Studies

Molecular docking studies were conducted for the receptor peroxisome proliferator-activated receptor-gamma (PPARγ). The three dimensional X-ray crystal structure of PPARγ was retrieved from Protein Data Bank (PDB) using the accession ID: 5Y2T with a resolution of 1.70 Å. The structure of complex DDBDG was modeled using ChemSketch and converted into a three dimensional structure. The chemical structures of Erlotinib (CID176870), Sorafenib (CID216239) and Rosiglitazone (CID77999) were retrieved from PubChem database. The receptor (PPARγ) was docked with the selected compounds using AutoDock4.2 software. Docking experiment was performed using Lamarckian Genetic Algorithm, with an initial population of 250 randomly placed individuals, a maximum number of 106 energy evaluations, a mutation rate of 0.02, and a crossover rate of 0.8. Conformation clustering was done considering root mean square deviation (RMSD) cut-off of 2.0 Å were clustered and the most favorable conformation was represented by the lowest free energy of binding (ΔG). To ensure that the binding pose of the docked compound represents favorable and valid potential binding mode, the docking parameter and method was validated by redocking the co-crystal ligand against the target protein.

Figure 5:
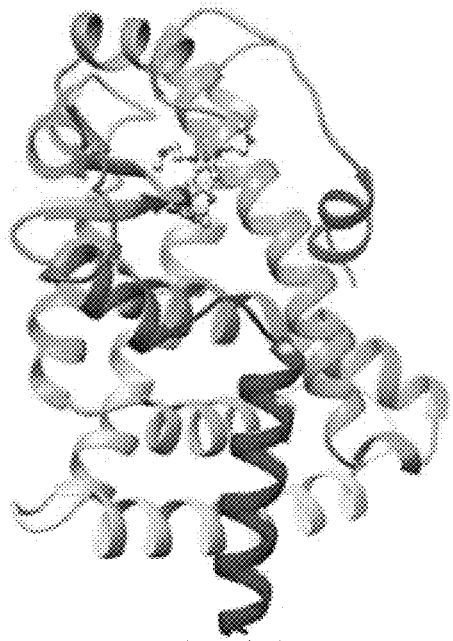
FIG. 5 shows binding modes of Erlotinib, Sorafenib, Rosiglitazone and gold complex (DDBDG) when docked with the receptor peroxisome proliferator-activated receptor-gamma (PPARγ), wherein the gold complex is as per an exemplary embodiment of the present disclosure.
Figure 5:
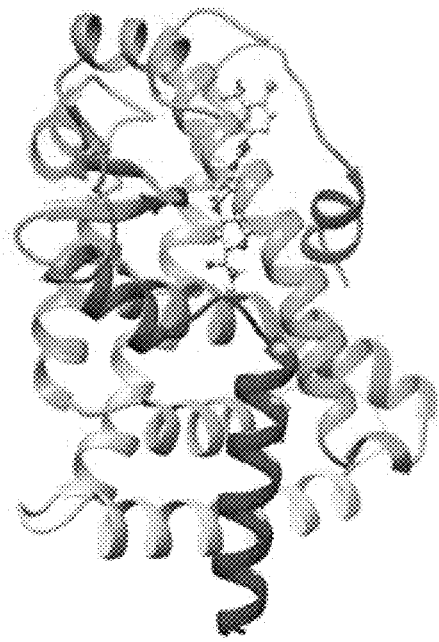
Figure 5:
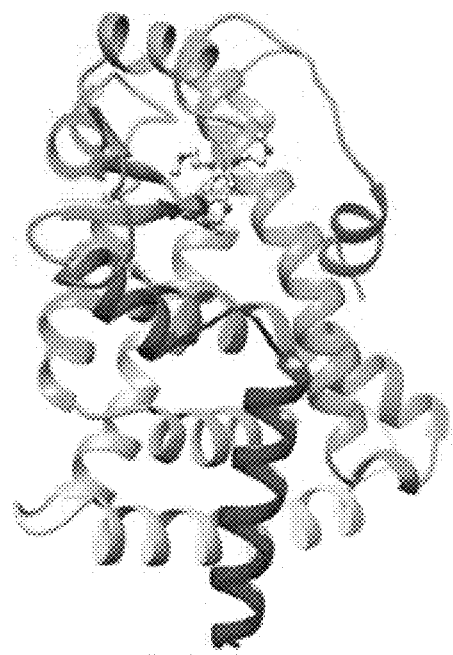
Figure 5:
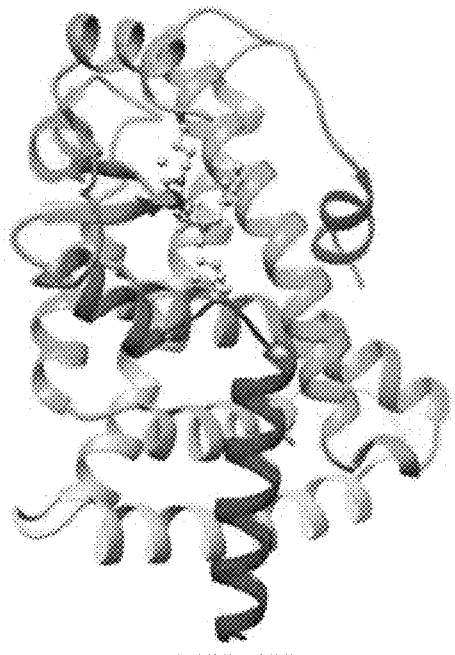

In molecular docking analysis, the root mean square deviation (RMSD) between the co-crystal and docked conformation was found to be <2 Å (1.484 Å). The redocking result confirmed that the compound was bound to its protein target very close to the true conformation indicating the reliability of the docking protocol and parameter. The binding modes of the docked compounds are shown in FIG. 5. Comparing the binding energies of the docked compounds, DDBDG exhibited the highest binding affinity with the target protein (Table 4). The protein-ligand complexes were also evaluated for non-bonded contacts and hydrogen bonds. DDBDG interacts with PPARγ by establishing one hydrogen bond with Ser342 and non-bonded contacts involving residues—Glu295, Leu228, Leu330, Leu333, Met348, Leu340, Ile341, Arg288, Glu343, Glu291, Cys285, Ile281, Gly284 and Phe287. Overall, DDBDG showed comparatively more interaction sites with PPARγ as compared to interaction sites between positive controls and PPARγ (Table 5).

TABLE 4

Binding energies of compounds docked with PPARγ

| Compound | Binding Energy (kCal/mol) |
| --- | --- |
| Erlotinib | −6.69 |
| Sorafenib | −8.67 |
| Rosiglitazone | −8.06 |

TABLE 4-continued

Binding energies of compounds docked with PPARγ

| Compound | Binding Energy (kCal/mol) |
| --- | --- |
| DDBDG | −10.54 |
| Cocrystal ligand | −10.34 |

TABLE 5

Molecular interaction profile of compounds docked with PPARγ

| Compound | Residues in non-bonded contacts | Residues in hydrogen bonds |
| --- | --- | --- |
| Erlotinib | Cys285, Ile281, Gly284, Phe287, Met354, Arg288, Leu330, Val339, Leu340, Ile341, Glu343 | Ser342 |
| Sorafenib | Ser289, Cys285, Arg288, Leu330, Met364, Arg280, Met348, Leu255, Ile249 | Nil |
| Rosiglitazone | Tyr473, His323, His449, Cys285, Gly284, Leu330, Met364, Leu353, Ile341, Met348 | Ser289 |
| DDBDG | Glu295, Leu228, Leu330, Leu333, Met348, Leu340, Ile341, Arg288, Glu343, Glu291, Cys285, Ile281, Gly284, Phe287 | Ser342 |
| Cocrystal ligand | Tyr473, Ile326, Leu330, Gln286, Cys285, Phe282, Arg288, Ile281, Gly284, Ile341, Arg280, Met348, Leu255 | Ser289, His323, His449 |

Example 7: Physicochemical and Pharmacokinetic Properties Analysis

Various physicochemical properties such as drug-like properties and toxicities of the selected compounds were evaluated in-silico using Data Warrior version 3.12.1 software [Sander T, Freyss J, von Korff M, Rufener C. DataWarrior: an open-source program for chemistry aware data visualization and analysis. J Chem Inform Model 2015; 55:460-473]. The pharmacokinetic properties of the molecules 5 were calculated using SwissADME [Daina A, Michielin O, Zoete V. SwissADME: a free web tool to evaluate pharmacokinetics, drug-likeness and medicinal chemistry friendliness of small molecules. SciRep 2017; 7:1-13]. The results of physiochemical, pharmacokinetic and toxicological properties using in-silico approaches showed that DDBDG is neither an irritant nor has any mutagenic, 10 tumorigenic and reproductive toxicity. Its gastrointestinal absorption is low and it does not cross blood brain barrier.

TABLE 6

Physicochemical and pharmacokinetic properties

| Property | DDBDG | Erlotinib | Sorafenib | Rosiglitazone |
| --- | --- | --- | --- | --- |
| Molecular weight | 681.593 | 393.442 | 464.83 | 357.433 |
| LogP (partition coefficient between n-octane and water) | 4.841 | 3.071 | 4.142 | 2.161 |
| LogS (aqueous solubility at 25° and pH = 7.5) | −5.343 | −3.527 | −6.689 | −3.666 |
| Hydrogen bond acceptor | 5 | 7 | 7 | 6 |
| Hydrogen bond donor | 0 | 1 | 3 | 1 |
| Rotatable bonds | 8 | 10 | 6 | 7 |
| Topological polar surface area | 120.55 | 74.73 | 92.35 | 96.83 |
| Drug likeness | −0.890 | −5.971 | −5.118 | 7.503 |
| Mutagenic | None | None | None | None |
| Tumorigenic | None | None | None | None |
| Reproductive toxicity | None | None | None | None |

TABLE 6-continued

Physicochemical and pharmacokinetic properties

| Property | DDBDG | Erlotinib | Sorafenib | Rosiglitazone |
|---|---|---|---|---|
| Irritant | None | None | None | None |
| Gastrointestinal absorption | Low | High | Low | High |
| Blood brain barrier permeability | No | Yes | No | No |
| P-glycoprotein substrate | Yes | No | No | No |
| CYP1A2 inhibitor | No | Yes | Yes | No |
| CYP2C19 inhibitor | Yes | Yes | Yes | Yes |
| CYP2C9 inhibitor | Yes | Yes | Yes | Yes |
| CYP2D6 inhibitor | No | Yes | Yes | Yes |
| CYP3A4 inhibitor | Yes | Yes | Yes | Yes |

The foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Advantages of the Present Invention

The present disclosure provides complexes with high therapeutic efficacy in cancer cells and low toxicity in normal cells.

The present disclosure provides complexes with multi-targeted therapeutic approach including cell apoptosis, disruption of mitochondrial membrane potential, and increase in oxidative stress.

The invention claimed is:

1. An anti-cancer gold complex of Formula I, a stereoisomer, a pharmaceutically acceptable salt or a pharmaceutically acceptable solvate thereof:

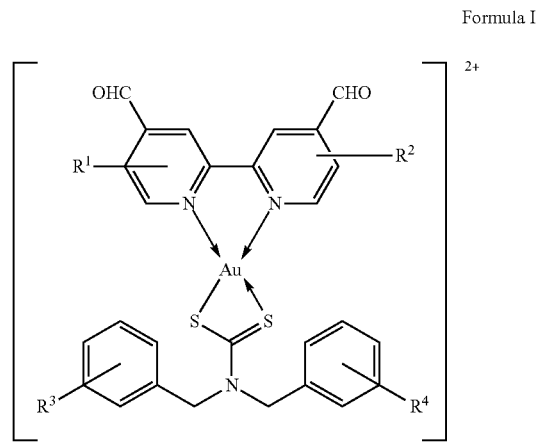

Formula I wherein $R^1$, $R^2$, $R^3$ and $R^4$ is independently selected from one or more of H, —OH, $C_{1-6}$ alkoxy, $C_{1-6}$ alkyl, halogen, nitro, amino, —COOH, —($C_{6-10}$)aryl and —($C_{4-14}$)heterocyclyl.

2. The complex as claimed in claim 1, wherein $R^1$, $R^2$, $R^3$ and $R^4$ is independently selected from one or more of H, —OH, —OCH$_3$, —OC$_2$H$_5$, —CH$_3$, —C$_2$H$_5$, Cl, Br, nitro, amino, phenyl, and —COOH.

3. The complex as claimed in claim 1, wherein the complex is dibenzyldithiocarbamato 2,2'-bipyridine-4,4'-dicarboxaldehyde gold (III).

4. A pharmaceutical composition comprising an anti-cancer gold complex of Formula I, a stereoisomer, a pharmaceutically acceptable salt or a pharmaceutically acceptable solvate thereof as claimed in claim 1.

5. The composition as claimed in claim 4, wherein the composition is a tablet, gel, capsule, solution, granules, powder, lozenge, suspension, suppositories, nanoparticles, oil, microparticles, or paste.

6. An anti-cancer gold complex of Formula I, a stereoisomer, a pharmaceutically acceptable salt or a pharmaceutically acceptable solvate thereof as claimed in claim 1 for the treatment of cancer.

7. A process of synthesis of an anti-cancer gold complex of the Formula I, a stereoisomer, a pharmaceutically acceptable salt or a pharmaceutically acceptable solvate thereof as claimed in claim 1, the process comprising the steps of: (a) mixing 2,2'-bipyridine-4,4'-dicarboxaldehyde compound (2) with Au(III) salt (3) in a solvent to generate a compound (4); and (b) adding and stirring a sodium dithiocarbamate compound (5) into the solution of step (a) to give a complex of Formula I,

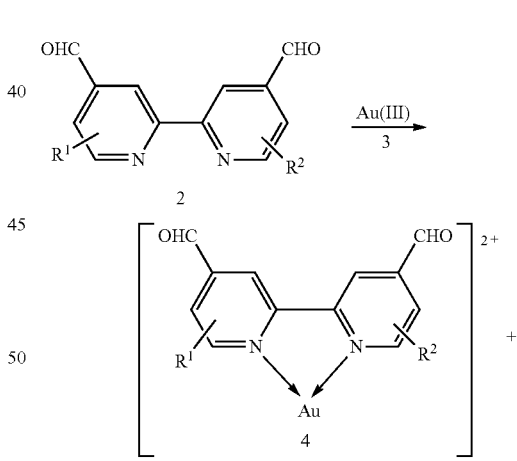

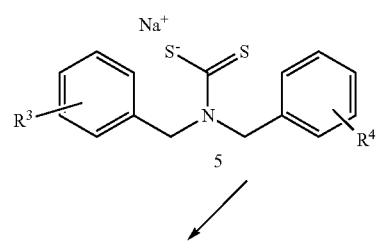

-continued

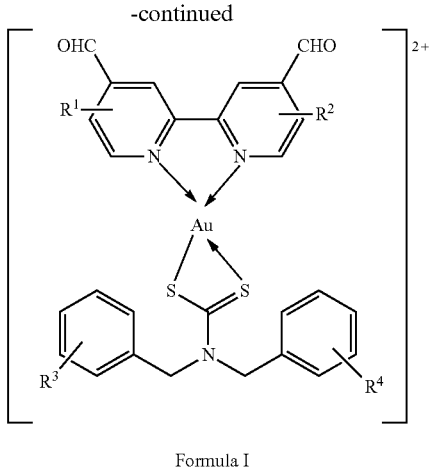

Formula I wherein $R^1$, $R^2$, $R^3$ and $R^4$ is independently selected from one or more of H, —OH, $C_{1-6}$ alkoxy, $C_{1-6}$ alkyl, halogen, nitro, amino, —COOH, —$(C_{6-10})$aryl and —$(C_{4-14})$heterocyclyl.

8. The process as claimed in claim 7, wherein the solvent is selected from ethanol, methanol, water, propanol, dimethyl sulphoxide, and combinations thereof.

9. The process as claimed in claim 7, wherein the Au(III) salt is selected from sodium tetrachloroaurate, potassium tetrachloroaurate, sodium tetracyanoaurate, potassium tetracyanoaurate, and combinations thereof.

10. A method of treating a cancer by comprising administering a therapeutically effective amount of an anti-cancer gold complex of Formula I, a stereoisomer, a pharmaceutically acceptable salt or a pharmaceutically acceptable solvate thereof as claimed in claim 1 to a subject in need thereof.

11. The method as claimed in claim 10, wherein the therapeutically effective amount is about 0.01 to 100 mg/kg of the complex per kg weight of the subject.

12. The method as claimed in claim 10, wherein the cancer is breast cancer, rectal cancer, prostrate cancer, brain cancer, ovarian cancer, lung cancer, colorectal cancer, colon cancer, multiple myeloma, leukemia, cervical cancer, stomach cancer, skin cancer, thyroid cancer, testicular cancer, bone cancer, bladder cancer, intestinal cancer, or pancreatic cancer.

* * * * *